(12) United States Patent
Nesterenko et al.

(10) Patent No.: US 11,945,760 B2
(45) Date of Patent: Apr. 2, 2024

(54) PROCESS FOR CONVERTING ONE OR MORE METHYL HALIDES INTO ETHYLENE AND PROPYLENE

(71) Applicants: TOTALENERGIES ONETECH, Courbevoie (FR); SULZER MANAGEMENT AG, Winterthur (CH)

(72) Inventors: Nikolai Nesterenko, Nivelles (BE); Gleb Veryasov, Nivelles (BE); Raoul Dethier, Schaerbeek (BE); Romuald Coupan, Vanves (FR)

(73) Assignees: TOTALENERGIES ONETECH, Courbevoie (FR); SULZER MANAGEMENT AG, Winterthur (CH)

( * ) Notice: Subject to any disclaimer, the term of this patent is extended or adjusted under 35 U.S.C. 154(b) by 0 days.

(21) Appl. No.: 17/777,924

(22) PCT Filed: Nov. 20, 2020

(86) PCT No.: PCT/EP2020/082842
§ 371 (c)(1),
(2) Date: May 18, 2022

(87) PCT Pub. No.: WO2021/099548
PCT Pub. Date: May 27, 2021

(65) Prior Publication Data
US 2022/0411350 A1 Dec. 29, 2022

(30) Foreign Application Priority Data
Nov. 22, 2019 (EP) ..................................... 19315143

(51) Int. Cl.
*C07C 1/30* (2006.01)
*B01J 23/02* (2006.01)
(Continued)

(52) U.S. Cl.
CPC .................. *C07C 1/30* (2013.01); *B01J 23/02* (2013.01); *C07C 11/04* (2013.01); *C07C 11/06* (2013.01)

(58) Field of Classification Search
CPC ................ C07C 1/30; C07C 4/00; C07C 4/06
See application file for complete search history.

(56) References Cited

U.S. PATENT DOCUMENTS 7,317,133 B2 * 1/2008 Vora .......................... C07C 4/06
585/653
2008/0188701 A1 8/2008 Qi et al.
(Continued)

FOREIGN PATENT DOCUMENTS

EP 1035915 A1 9/2000
EP 1036136 A1 9/2000
(Continued)

OTHER PUBLICATIONS

International Search Report and Written Opinion issued in Application No. PCT/EP2020/082842 dated Feb. 10, 2021; 13 pages.
(Continued)

*Primary Examiner* — Sharon Pregler
(74) *Attorney, Agent, or Firm* — Ewing & Jones, PLLC (57) ABSTRACT

The present disclosure concerns a process for converting methyl halides to ethylene and propylene, said process comprising the steps of (a) providing a feedstream comprising methyl halides; (b) providing a first and second catalyst composition, said second catalyst composition comprising a cracking catalyst; (c) contacting said feedstream with said first catalyst composition in a first reaction zone under first reaction conditions to provide a first product stream; and (d) subjecting at least a part of said first product stream to an Olefin Catalytic Cracking with said second catalyst composition in a second reaction zone under second reaction conditions to provide a second product steam. The process (Continued)

is remarkable in that said step (c) is performed under 400° C., and in that said first catalyst composition comprises molecular sieves with a Si/Al atomic between 2 and 18 and with a plurality of pores with a shape of an 8-membered ring or less.

13 Claims, 4 Drawing Sheets

(51) Int. Cl.
  *C07C 11/04* (2006.01)
  *C07C 11/06* (2006.01)

(56) References Cited

U.S. PATENT DOCUMENTS

| | | |
|---|---|---|
| 2010/0087686 A1 | 4/2010 | Fong et al. |
| 2015/0274608 A1* | 10/2015 | Nesterenko .............. C07C 1/322 585/324 |
| 2016/0200642 A1 | 7/2016 | Ghosh et al. |
| 2016/0347681 A1 | 12/2016 | Ghosh et al. |
| 2016/0347682 A1* | 12/2016 | Ghosh ....................... C07C 1/26 |
| 2016/0362349 A1* | 12/2016 | Ghosh ....................... B01J 37/28 |
| 2017/0057886 A1* | 3/2017 | Fickel ....................... C07C 1/30 |

FOREIGN PATENT DOCUMENTS

| | | |
|---|---|---|
| EP | 1036135 B1 | 9/2002 |
| EP | 1036137 B1 | 11/2002 |
| EP | 1036139 B1 | 11/2002 |
| EP | 1190015 B1 | 1/2003 |
| EP | 1036134 B1 | 4/2003 |
| EP | 1036138 B1 | 5/2003 |
| EP | 1036133 B1 | 7/2003 |
| EP | 1194500 B1 | 8/2003 |
| EP | 1363983 A1 | 11/2003 |
| EP | 1194502 B1 | 8/2006 |
| WO | 2004048299 A2 | 6/2004 |
| WO | 2016099775 A1 | 6/2016 |
| WO | 2018187141 A1 | 10/2018 |

OTHER PUBLICATIONS

Ch. Baerlocher et al., "Atlas of Zeolite Framework Types", 6th revised edition, 2007, Elsevier.

* cited by examiner

PROCESS FOR CONVERTING ONE OR MORE METHYL HALIDES INTO ETHYLENE AND PROPYLENE

CROSS-REFERENCE TO RELATED APPLICATIONS

This application claims the benefit of PCT/EP2020/082842 filed Nov. 20, 2020, which claims priority from EP 19315143.8 filed Nov. 22, 2019, which are incorporated herein by reference in their entireties for all purposes.

FIELD OF THE DISCLOSURE

The present disclosure relates to a process for converting one or more methyl halides selectively into ethylene and propylene.

BACKGROUND OF THE DISCLOSURE

Olefins are considered to be key components of the chemical industry. Starting from alkanes, and methane in particular, it is feasible to obtain the corresponding alkyl halide, for example, methyl halide. Alkyl halide can be then transformed into olefins. By adjusting the reaction conditions and employing a specific catalyst, the ratios of these various olefins may be modified, leading to the obtaining of the desired effluents, that can be then separated by known technology. The process for converting one or more alkyl halides into olefins, namely the second step of the two-step process for producing olefins from alkanes, has already been thoroughly studied.

In US 2016/0347681, 10-membered ring-containing HZMS-5 zeolite having a silica-to-alumina ratio (SAR) comprised between 25 and 500 allows for converting methyl chloride at 350° C. with selectivity to ethylene and propylene of 38.2% and with conversion of 35.1% after 20 hours on stream. When HZMS-5 was ion-exchanged to MgZMS-5, the conversion was increased to 99.8% but the selectivity dropped to 25.9%. A significant amount of C4 olefins was formed in both cases. In US 2016/0200642, HZMS-5 zeolite presenting a SAR of 1192 has been used. After 20 hours on stream, the selectivity to ethylene and propylene was increased to 66.7%, while the selectivity to C4 olefins reaches 21.7% and to C5+ olefins reaches 7.4%. Under these conditions, no aromatics were generated.

In US 2016/0347682, a crystalline zeolite catalyst having an STI framework topology, such as SSZ-75, was used for the conversion of an alkyl halide to olefins. In some aspects, this catalyst has shown, under reaction temperature ranging between 300° C. and 500° C., a selectivity to ethylene and propylene ranging from 70% to 90%. Besides the light olefins, the reaction produces by-products such as methane, C4-C5 olefins and BTX (benzene, toluene and xylene).

US 2008/0188701 describes the use of a silicoaluminophosphate molecular sieve catalyst, which comprises 50 wt. % of SAPO-34 molecular sieve as active component and 50 wt. % of alumina as the matrix. At a temperature of 450° C., methyl chloride, diluted with methanol in a ratio methanol/methyl chloride of 0.1:1, was converted in a fixed bed reactor with 2 grams of catalyst at 77.89% and afforded a selectivity to ethylene and propylene of 84.35% after 1 hour. Formation of C4 olefins amounts to 10.47%. However, when the reaction was conducted into a fluidized bed reactor with 75 grams of a catalyst prepared by the spray drying process, the conversion decreases to 72.78%, but the selectivity to ethylene and propylene increases to 87.59%. Formation of C4 olefins diminishes to 7.99%.

In US 2017/0057886, an aluminosilicate zeolite catalyst, i.e. a chabazite zeolite of the SSZ-13 type having relatively small pore diameter which inhibits the molecule larger than those bearing four carbon atoms to exit its framework, has been used in the olefin production from methyl halide. It is described that in particular aspects, the combined maximum selectivity of ethylene, propylene and butylene is at least 85%. The selectivity in C4 alkenes ranges between 0% and 15% and the selectivity in aromatic compounds or in C2-C4 alkanes is less than 0.1%. In one instance, at a temperature of 450° C., the selectivity to ethylene and propylene was reported to be of 73.64% at a conversion of 99.65%. However, after less than 1.5 hours on stream, the catalyst gets deactivated, dropping the conversion to less than 20% after 3 hours on stream.

In WO 2016/099775, the methyl chloride transformation into olefins was studied with a SAPO zeolite catalyst. After 20 h on stream, a conversion of 34.5% was achieved and a selectivity to ethylene and propylene of 90.7% was observed. 5.0% of C4 olefins was generated.

It is admitted that any unreacted alkyl halide can be recycled and reintroduced in the alkyl halide feed to further maximize the overall conversion of alkyl halides to olefins. It is also admitted that separation steps have also to be considered for removing C4+ olefins in order to transform them into ethylene and propylene in additional processes. These considerations have resulted in the establishment of integrated processes in order to produce ethylene and propylene from alkyl halide.

In US 2010/0087686, an integrated process for producing aromatic hydrocarbons, ethylene and/or propylene from methane is described. Methane is first transformed in methyl bromide which is, in a second step, converted into higher molecular hydrocarbons. Using a coupling catalyst, for instance, zeolite with a dopant (i.e. manganese), an effluent comprising 32% of aromatics (i.e. benzene, toluene and xylenes) and thus only 68% of C2-C5 alkanes, with a minor content of C2-C5 alkenes, methane and hydrogen bromide, is produced. The zeolite catalyst is described as being gradually deactivated by the formation of coke. Distillation steps are carried out to separate the aromatics and the C2-C5 alkanes (with also methane, hydrogen bromide and a minor concentration of C2-C5 alkenes). The aromatics are further processed to produce benzene and p-xylene, which are separated. The stream containing the C2-C5 linear alkanes (and a minor amount of C2-C5 alkenes) is first purified in order to remove hydrogen bromide and methane before being cracked to produce pure ethylene and pure propylene after a final separation step. Nevertheless, the important number of aromatics produced, 32%, reduces considerably the efficiency of the further treatments (numerous separation steps before and after the cracking step itself). Indeed, each of the further step is susceptible to reduce the overall yield in ethylene and propylene.

In WO 2018/187141, a zeolite with a CHA framework and having a Si/Al molar ratio ranging between 50 and 150 is described as suitable to convert methyl halides into C2-C4 olefins.

Starting from an alkyl halide and wishing to obtain ethylene and propylene is thus not straightforward. In processes converting alkyl halide into olefins, a large amount of by-products (notably aromatics and coke) is formed, reducing thus the number of products that need to undertake an additional step, for instance, a pre-conversion of the alkyl halide at a lower temperature to the olefinic hydrocarbons stream before the cracking step. One should also mention that this cracking step is typically performed at high temperature (>500° C.), which may lead to a partial thermal disproportionation of the alkyl halide to alkyl di-halide and $CH_4$. As a consequence, the formed alkyl di-halide transforms to heavy aromatics and may cause reactor plugging. The facility to form alkyl halide increases in the series F<Cl<Br<I. starting from Br, the direct processing of the alky halide is practically impossible and required a pre-conversion step. However, if a methyl halide (e.g., $CH_3Br$) is present in a mixture with olefins, the formation of coke is mitigated and the carbon from $CH_3Br$ is substantially incorporated in the olefins pool. This means that the $CH_3Br$ should be pre-converted partially or fully to hydrocarbons at low temperature or subjected to high-temperature conversion zone only in the presence of heavier hydrocarbons.

The present disclosure has thus the objective of increasing the amount of the intermediate products in a process involving at least one step of cracking for the conversion of one or more methyl halides into ethylene and propylene

SUMMARY OF THE DISCLOSURE

According to a first aspect, the disclosure provides a process for converting one or more methyl halides to ethylene and propylene, said process comprising the following steps:
a) providing a feedstream comprising one or more methyl halides; optionally, diluted in at least one diluent;
b) providing a first catalyst composition and a second catalyst composition, said second catalyst composition comprising a cracking catalyst;
c) contacting said feedstream with said first catalyst composition in a first reaction zone under first reaction conditions to provide a first product stream; and
d) subjecting at least a part of said first product stream to an Olefin Catalytic Cracking (OCC) with said second catalyst composition in a second reaction zone under second reaction conditions to provide a second product steam,
the process is remarkable in that said first reaction conditions include a reaction temperature below 400° C., and in that said first catalyst composition comprises one or more molecular sieves with a Si/Al atomic ratio ranging from 2 to 18, wherein said one or more molecular sieves comprise a plurality of pores with a shape of an 8-membered ring or less and further wherein said one or more molecular sieves in the first catalyst composition are selected from the group of AEI, CHA, DDR, ERI, KFI, and LEV families and any mixture thereof.

The group of AEI, CHA, DDR, ERI, KFI, and LEV families are molecular sieves comprising at least one cage and at least one channel, wherein said at least one cage and said at least one channel have each an opening, the opening of the cage being greater than the opening of the channel.

With preference, step (d) comprises subjecting said first product stream in totality, without conducting a separation step, to an Olefin Catalytic Cracking (OCC) with said second catalyst composition in a second reaction zone under second reaction conditions to provide a second product steam.

The first and second catalyst compositions can be the same or different; preferably, the first and second catalyst compositions are different.

Surprisingly, it has been found that both a high selectivity to acyclic C3-C6 olefins and a high conversion can be achieved with the use of a first catalyst composition comprising molecular sieves with a Si/Al atomic ratio ranging from 2 to 18, with a plurality of pores, the biggest of said pores being an 8-membered ring and with cage(s) bigger than channel(s). According to the disclosure the molecular sieves with a Si/Al atomic ratio ranging from 5 to 18 with cage(s) bigger than channel(s) are selected from the group of AEI, CHA, DDR, ERI, KFI, and LEV families and any mixture thereof.

It was found that the use of molecular sieve having a Si/Al atomic ratio from 2 to 18 (SAR from 4 to 36), preferably from 5 to 18 or from 5 to 15, of a specific structure with pores having a shape of an 8-membered ring or less allows for steadily transforming methyl halides into non-cyclic C3-C6 olefins for at least 24 hours. With such process, after the cracking step, the selectivity into ethylene and propylene is above 75% while the selectivity into aromatics has been lowered to less than 10%, preferably to less than 7%, more preferably to less than 6%.

Without wishing to be bound by any theory, a person skilled in the art will see a difference in the reaction mechanism observed on that system relative to the one described in the literature. All the known small molecular sieves showed the selectivity typical to the 'hydrocarbon pool' mechanism, which is well described in the literature. This disclosure shows that in case of using a particular molecular sieve with the optimal Si/Al atomic ratio, the transformation of a methyl halide ($CH_3X$) could be performed via oligo-dehydrohalogenation mechanism (homologation followed by subtraction of HX). The advantage of this reaction pathway is a very low formation of coke and high catalyst stability. The catalyst is suitable for the conventionally fixed bed operation and produced only a very little amount of ethylene.

The production of olefins higher than C4 is a surprising result of the disclosure as US2017/0057886 was teaching that the production of olefins higher than C4 was inhibited by the use of a small pore zeolite, i.e. a zeolite with a pore size inferior to 4 Å.

In consequence, the amount of intermediate products for providing ethylene and propylene from one or more methyl halides as starting material is considerably increased with the process of the present disclosure.

With preference, one or more of the following embodiments can be used to better define the first catalyst composition used in the process:
The one or more molecular sieves are selected from one or more silico aluminophosphates and/or one or more zeolites, preferably the one or more molecular sieves are one or more zeolites.
The one or more molecular sieves are exchanged with two-valent cations.
The one or more molecular sieves are steamed. This allows the one or more molecular sieves of the catalyst composition to have a Si/Al atomic ratio ranging from 2 to 18, more preferably from 5 to 18 or from 5 to 15.
The one or more molecular sieves are exchanged with two-valent cations and steamed.
The preferred molecular sieves from the AEI family are one or more of SSZ-39, ALPO-18 or SAPO-18, more preferably SSZ-39.
The preferred molecular sieves from the CHA family are one or more of chabazite, SSZ-13, SAPO-44, SSZ-62 or SAPO-34, more preferably SSZ-13.
The preferred molecular sieves from the DDR family are one or more of ZSM-58 or Sigma-1.
The preferred molecular sieves from the ERI family are one or more of erionite or UZM-12.

The preferred molecular sieve from KFI family is ZK-5.
The preferred molecular sieves from the LEV family are one or more of SAPO-35, levyne, ZK-20, SSZ-17 or NU-3.
The one or more molecular sieves have an average pore size diameter of at most 4.2 Å, as determined by BET (Brunauer-Emmet-Teller) experiments; preferably of 3.8 Å.
The first catalyst composition contains one or more alkaline earth metal-containing materials. Said one or more alkaline earth metal-containing materials are selected from the group of beryllium, magnesium, calcium, strontium, barium, and any mixtures thereof.
The first catalyst composition further comprises from 1 to 50 wt. % of hydrotalcite as based on the total weight of the first catalyst composition; preferably from 5 to 25 wt. %, more preferably from 7 to 23 wt. %, even more preferably from 10 to 20 wt. %.
The one or more molecular sieves after or before steaming are doped with one or more phosphorus-containing materials, so as to form a phosphate molecular sieve. With preference, said phosphate molecular sieve can be further subjected to a steaming step.
The first catalyst composition comprises between 0.1 wt. % and 7.0 wt. % of one or more phosphorus-containing materials as based on the total weight of the first catalyst composition, preferably between 0.3 wt. % and 4.5 wt. %, preferentially between 0.5 wt. % and 4.0 wt. %, more preferentially 2.0 wt. %.
The one or more molecular sieves are doped with one or more phosphorus-containing materials and with one or more alkaline earth metal-containing materials, preferably a magnesium or calcium-containing material.
The first catalyst composition further comprises a binder; with preference said binder is one or more selected from the group of silica, alpha-alumina, clays, alumina phosphates, calcium phosphates, magnesium phosphates, and mullite; more preferentially, silica.
The catalyst composition further comprises a binder; and the binder is present in an amount of at least 10 wt. % as based on the total weight of the first catalyst composition; preferably in an amount of at least 20 wt. %, most preferably in an amount of at least 30 wt. %, even more preferably in an amount of at least 40 wt. %, and most preferably in an amount of at least 50 wt. %.
One or more molecular sieves of the first catalyst composition are transition metal-free. With preference, the one or more molecular sieves contain less than 1000 wt. ppm of noble metal as determined by XRF and/or less than 1 wt. % of transition metals as determined by XRF based on the total weight of the one or more molecular sieves; with preference, the content of the transition metals is below 1.0 wt. %, preferably below 1000 wt.ppm. Traces of these metals may be present on the catalyst as impurities from the binder, e.g. a component of the clays.
The one or more molecular sieves are alkali metal-free. With preference, the one or more molecular sieves contain less than 1 wt. % of alkali metals as determined by XRF based on the total weight of the one or more molecular sieves, more preferably below 0.5 wt. %.
At least 50 wt. % of said one or more molecular sieves are in their hydrogen form as based on the total weight of the one or more molecular sieves, preferentially at least 60 wt. %, more preferentially at least 70 wt. %, even more preferentially at least 80% and most preferentially at least 90%. It can be that 99.9 wt. % of said one or more molecular sieves are in their hydrogen form as based on the total weight of the one or more molecular sieves.

With preference, one step of steaming is carried out before step (c) at a temperature ranging from 400° C. to 1000° C., more preferentially at a temperature ranging from 600° C. to 800° C. Steaming allows for the removal of a large fraction of aluminium from the lattice, which subsequently leads to an adjustment of the Si/Al atomic ratio.

With preference, the first catalyst composition is calcinated before said step (c) of contacting the feedstream; with preference, the first catalyst composition is calcined at a temperature of at least 400° C.

With preference, one or more of the following embodiments can be used to better define the second catalyst composition used in the process:
The one or more molecular sieves are selected from one or more silico aluminophosphates and/or one or more zeolites, preferably the one or more molecular sieves are one or more zeolites.
Said cracking catalyst comprises one or more molecular sieves and/or one or more clays; with preference, said cracking catalyst comprises one or more molecular sieves selected from silicalites from the MFI family, crystalline silicate from the MFI family with a Si/Al atomic ratio of at least 180, crystalline silicate from the MEL family with a Si/Al atomic ratio ranging between 150 and 800, and/or phosphorous-modified molecular sieve from the MFI, MEL, FER, or MOR family. More preferably, said cracking catalyst comprises one or more molecular sieves selected from silicalites from the MFI family, optionally with a silica binder.
Said cracking catalyst comprises one or more molecular sieves with a binder; preferably, a silica binder.
Said cracking catalyst can be subjected to a steaming step before step (d).
The process can be carried out in one or more fixed bed reactor and/or in one or more fluidized bed reactor.
In an embodiment wherein the process is carried out in one reactor, said reactor comprises at least a first reaction zone and a second reaction zone, the second reaction zone being downstream of the first reaction zone, and the first catalyst composition is provided into the first reaction zone and the second catalyst composition is provided into the second reaction zone.
In an embodiment wherein the process is carried out in one reactor comprising at least two vessels, the first catalyst composition is provided into a first vessel of one reactor forming a first reaction zone, and the second catalyst composition is provided in a second vessel of said one reactor forming a second reaction zone, said second vessel being downstream of said first vessel.
In an embodiment wherein the process is carried out in at least two reactors, the first catalyst composition is provided into a first reactor forming a first reaction zone, and the second catalyst composition is provided into a second reactor forming a second reaction zone, the second reactor being downstream of the first reactor and fluidly connected to the first reactor.

With preference, one or more of the following embodiments can be used to better define the step (a) of the process:
The one or more methyl halides in the feedstream of step (a) comprise one or more monohalo-methyl.
The one or more methyl halides in the feedstream of step (a) are or comprise methyl bromide.
The one or more methyl halides in the feedstream of step (a) comprise one or more monohalo-methyl with at most 10 wt. % of polyhalo-methyl, such as dihalo-methyl, trihalo-methyl and/or tetrahalo-methyl.

The one or more methyl halides in the feedstream of step (a) comprise a mixture of one or more selected from monohalo-methyl, dihalo-methyl, trihalo-methyl and/or tetrahalo-methyl; with preference, the mixture comprises the monohalo-methyl in an amount of at least 90 wt. % of said mixture.

The halogen of said methyl halides, or of said monohalo-methyl, dihalo-methyl, trihalo-methyl or tetrahalo-methyl is selected from fluorine, chlorine, bromine, iodine and/or any mixture thereof, preferentially bromine.

The one or more methyl halides in the feedstream of step (a) comprise at least 50 wt. % of bromine as based on the total weight of said one or more methyl halides, preferentially at least 60 wt. %, more preferentially at least 70 wt. %, even more preferentially at least 80 wt. %, most preferentially at least 90 wt. %, even most preferentially 100 wt. %.

The feedstream of one or more methyl halides is diluted in a diluent, the molar ratio diluent/one or more methyl halides ranging between 2 and 20, preferentially between 3 and 10.

The feedstream of one or more methyl halides is diluted in a diluent, the diluent is gaseous nitrogen, hydrogen halides, $H_2$, $CO_2$, non-converted $CH_4$, CO, $C_2H_6$, $C_3H_8$, and/or $C_4H_{10}$, more preferably gaseous nitrogen.

In the preferred embodiment, the feedstream of one or more methyl halides contains less than 500 ppm of water and water precursor compounds (alcohols, aldehydes, carboxylic acids).

With preference, one or more of the following embodiments can be used to better define the step (c) of the process:
  Step (c) has a conversion rate of at least 20% of the one or more methyl halides into hydrocarbons; with preference, of at least 30%.
  The reaction conditions of step (c) include a reaction temperature ranging from 220° C. to 390° C.; more preferably ranging from 280° C. to 380° C.
  The reaction conditions of step (c) include a reaction temperature that is below 390° C., preferably below 380° C.
  The reaction conditions of step (c) include a weight hourly space velocity of said one or more methyl halides comprised between 0.1 $h^{-1}$ and 100 $h^{-1}$, preferably comprised between 1.0 $h^{-1}$ and 15 $h^{-1}$, more preferably comprised between 1.5 $h^{-1}$ and 10 $h^{-1}$, even more preferably comprised between 2.0 $h^{-1}$ and 6.0 $h^{-1}$.
  The reaction conditions of step (c) include a pressure ranging from 10 kPa to 500 kPa, preferably ranging from 20 kPa to 300 kPa, more preferably ranging from 50 kPa to 200 kPa.

With preference, one or more of the following embodiments can be used to better define the step (d) of the process:
  The second reaction conditions of step (d) include a reaction temperature ranging from 500° C. to 600° C.; preferably ranging from 510° C. to 590° C., more preferably ranging from 520° C. to 580° C.
  The second reaction conditions of step (d) include a weight hourly space velocity comprised between 0.1 $h^{-1}$ and 100 $h^{-1}$, preferably comprised between 1 $h^{-1}$ and 15 $h^{-1}$, more preferably comprised between 1.5 $h^{-1}$ and 10 $h^{-1}$, even more preferably comprised between 2.0 $h^{-1}$ and 6.0 $h^{-1}$.
  The second reaction conditions of step (d) include a pressure ranging from 0.1 MPa to 2 MPa, preferably ranging from 0.2 to 1 MPa.

In one embodiment, the step (d) of contacting said first product stream with said second catalyst composition is followed by a step (e) of performing a separation of ethylene and propylene from the said second product stream. With preference, said separation further comprises separating from the second product stream a C4+ stream, and, optionally, an additional step of separating C8+ hydrocarbons and C4-C7 compounds from said C4+ stream is carried out, said C4-C7 compounds being preferentially recycled to the second reaction zone.

In one preferred embodiment, step (c) further comprises separating from the first product stream a C4+ stream and the step (d) comprises subjecting said C4+ stream to an Olefin Catalytic Cracking (OCC) with said second catalyst composition in a second reaction zone under second reaction conditions to provide a second product stream, said step (d) being optionally followed by a step (e) of performing a separation of ethylene and propylene from said second product stream, said step (e) preferentially comprising the following sub-steps:
  i. separating C8+ hydrocarbons from the said second product stream, so as to provide a C8+ hydrocarbons stream and a remaining stream from said second product stream;
  ii. performing a separation of ethylene and propylene from the remaining stream of the said second product stream.

In one preferred embodiment, the step (c) further comprises separating from the first product stream a C4+ stream and separating from said C4+ stream a high boiling point fraction and a low boiling point fraction; and the step (d) comprises subjecting said low boiling point fraction to an Olefin Catalytic Cracking (OCC) with said second catalyst composition in a second reaction zone under second reaction conditions to provide a second product stream, said step (d) being optionally followed by a step (e) of performing a separation of ethylene and propylene from said second product stream, said step (e) preferentially comprising the following sub-steps:
  i. separating from said second product stream the C4+ compounds, so as to provide a C4+ stream and a remaining stream from said second product stream;
  ii. performing a separation of ethylene and propylene from the remaining stream of the said second product stream.

In an embodiment, the step (d) further comprises reinjecting at least a part of said first product stream or of said a C4+ stream into the feedstream of step (a).

In an embodiment, step (c) further comprises separating from the first product stream in a C2=/C2 stream; with preference, the step (d) further comprises reinjecting at least a part of said C2=/C2 stream into the feedstream of step (a).

In an embodiment, said process further comprises one or more of the following sub-steps:
  i. removing hydrogen halide from said first product stream before the step (d) or from said second product stream after the step (d);
  ii. recovering at least a part of the unreacted one or more methyl halides before or after the step (d), preferentially followed by a step of reinjecting said at least a part of unreacted one or more methyl halides into the feedstream of step (a);

iii. removing aromatics from said first product stream before the step (d) or from said second product stream after the step (d).

According to a second aspect, the disclosure provides the use of a catalyst composition in a process for converting one or more methyl halides to ethylene and propylene according to the first aspect, wherein said catalyst composition is a first catalyst composition, remarkable in that said first catalyst composition comprises one or more molecular sieves with a Si/Al atomic ratio ranging from 2 to 18 preferably from 5 to 18, and wherein said one or more molecular sieves comprise a plurality of pores, wherein said pores have a shape of an 8-membered ring or less, wherein said one or more molecular sieves in the first catalyst composition are selected from the group of AEI, CHA, DDR, ERI, KFI, and LEV families and any mixture thereof; and further wherein said first catalyst composition is operated under first reaction conditions including a reaction temperature below 400° C.

With preference, the one or more molecular sieves with a Si/Al atomic ratio ranging from 5 to 15 and/or the one or more molecular sieves are one or more zeolites.

With preference, the one or more molecular sieves are selected from the group of AEI and/or CHA families.

DETAILED DESCRIPTION OF THE DISCLOSURE

For the purpose of the disclosure, the following definitions are given:

Zeolite codes (e.g., CHA . . . ) are defined according to the "*Atlas of Zeolite Framework Types*", 6$^{th}$ revised edition, 2007, Elsevier, to which the present application also makes reference.

The terms "alkane" or "alkanes" as used herein describe acyclic branched or unbranched hydrocarbons having the general formula $C_nH_{2n+2}$, and therefore consisting entirely of hydrogen atoms and saturated carbon atoms; see e.g. IUPAC. Compendium of Chemical Terminology, 2nd ed. (1997). The term "alkanes" accordingly describes unbranched alkanes ("normal-paraffins" or "n-paraffins" or "n-alkanes") and branched alkanes ("iso-paraffins" or "iso-alkanes") but excludes naphthenes (cycloalkanes).

The term "aromatic hydrocarbons" or "aromatics" relates to cyclically conjugated hydrocarbon with stability (due to derealization) that is significantly greater than that of a hypothetical localized structure (e.g. Kekule structure). The most common method for determining aromaticity of a given hydrocarbon is the observation of diatropicity in the $^1$H NMR spectrum.

The terms "olefin" or "alkene" as used herein relate to an unsaturated hydrocarbon compound containing at least one carbon-carbon double bond.

The terms "mono-olefin" as used herein relates to an unsaturated hydrocarbon compound containing one single carbon-carbon double bond.

As used herein, the term "C# hydrocarbons", wherein "#" is a positive integer, is meant to describe all hydrocarbons having # carbon atoms. C# hydrocarbons are sometimes indicated as just C#. Moreover, the term "C#+ hydrocarbons" is meant to describe all hydrocarbon molecules having # or more carbon atoms. Accordingly, the expression "C5+ hydrocarbons" is meant to describe a mixture of hydrocarbons having 5 or more carbon atoms.

The symbol "=" in the term "C#= hydrocarbon" indicates that the hydrocarbon concerned is an olefin or an alkene, the notation "=" symbolizing the carbon-carbon double bond.

The term "steam" is used to refer to water in the gas phase, which is formed when water boils.

The term "alkali metal" refers to an element classified as an element from group 1 of the periodic table of elements (or group IA), excluding hydrogen. According to this definition, the alkali metals are Li, Na, K, Rb, Cs and Fr.

The term "alkaline earth metal" refers to an element classified as an element from group 2 of the periodic table of elements (or group IIA). According to this definition, the alkaline earth metals are Be, Mg, Ca, Sr, Ba and Ra.

The term "transition metal" refers to an element whose atom has a partially filled d sub-shell, or which can give rise to cations with an incomplete d sub-shell (IUPAC definition) . According to this definition, the transition metals are Sc, Ti, V, Cr, Mn, Fe, Co, Ni, Cu, Zn, Y, Zr, Nb, Mo, Tc, Ru, Rh, Pd, Ag, Cd, Hf, Ta, W, Re, Os, Ir, Pt, Au, Hg, Ac, Rf, Db, Sg, Bh, Hs, Mt, Ds, Rg, and Cn. The term "transition metal" includes the group 12 elements i.e. Zn, Cd and Hg.

The yield to particular chemical compounds is determined as the mathematical product between the selectivity to said particular chemical compounds and the conversion rate of the chemical reaction. The mathematical product is expressed as a percentage.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all integer numbers and, where appropriate, fractions subsumed within that range (e.g. 1 to 5 can include 1, 2, 3, 4, 5 when referring to, for example, a number of elements, and can also include 1.5, 2, 2.75 and 3.80, when referring to, for example, measurements). The recitation of endpoints also includes the recited endpoint values themselves (e.g. from 1.0 to 5.0 includes both 1.0 and 5.0). Any numerical range recited herein is intended to include all sub-ranges subsumed therein.

The particular features, structures, characteristics or embodiments may be combined in any suitable manner, as would be apparent to a person skilled in the art from this disclosure, in one or more embodiments.

The disclosure provides a process for converting one or more methyl halides to ethylene and propylene, said process comprising the following steps:

a) providing a feedstream comprising one or more methyl halides; optionally, diluted in at least one diluent;

b) providing a first catalyst composition and a second catalyst composition, said second catalyst composition comprising a cracking catalyst;

c) contacting said feedstream with said first catalyst composition in a first reaction zone under first reaction conditions to provide a first product stream; and d) subjecting at least a part of said first product stream to an Olefin Catalytic Cracking (OCC) with said second catalyst composition in a second reaction zone under second reaction conditions to provide a second product steam according to the disclosure, the first reaction conditions include a reaction temperature below 400° C., and said first catalyst composition comprises one or more molecular sieves with a Si/Al atomic ratio ranging from 2 to 18, preferably from 5 to 18, wherein said one or more molecular sieves comprise a plurality of pores with a shape of an 8-membered ring or less and further wherein said one or more molecular sieves in the first catalyst composition are selected from the group of AEI, CHA, DDR, ERI, KFI, and LEV families and any mixture thereof.

Figure 1:
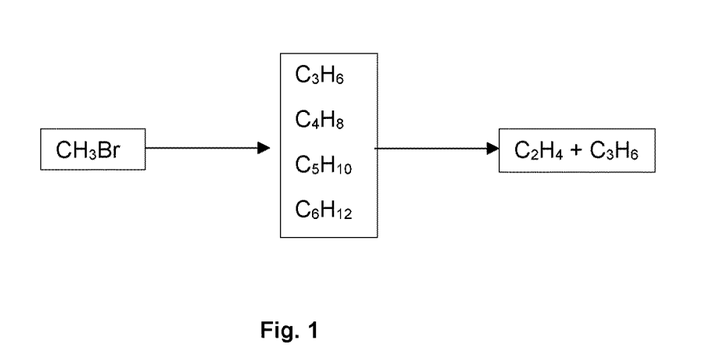
FIG. 1 schematically illustrates the process of the present disclosure

The two chemical reactions involved in the process according to the disclosure are schematically represented in FIG. 1.

The First Catalyst Composition

The one or more molecular sieves are selected from one or more silico aluminophosphates and/or one or more zeolites, preferably the one or more molecular sieves are one or more zeolites.

The one or more molecular sieves are selected from the group of AEI, CHA, DDR, ERI, KFI, and LEV families and any mixture thereof, preferably from the group of AEI and/or families.

For example, the molecular sieves from the AEI family are one or more of SSZ-39, ALPO-18 or SAPO-18, preferably SSZ-39. For example, the molecular sieves from the CHA family are one or more of chabazite, SSZ-13, SAPO-44, SSZ-62 or SAPO-34, more preferably SSZ-13.

For example, the molecular sieves from DDR family are one or more of ZSM-58 or Sigma-1. For example, the molecular sieves from the ERI family are one or more of erionite or UZM-12. For example, the molecular sieve from KFI family is ZK-5. For example, the molecular sieves from the LEV family are one or more of SAPO-35, levyne, ZK-20, SSZ-17 or NU-3.

To provide an appropriate acidity, it is preferred that the one or more molecular sieves are at least partly in their hydrogen form. Preferably more than 50 wt. % of the total amount of the one or more molecular sieves used are in their hydrogen form, preferably at least 80 wt. %, more preferably at least 90 wt. %, and even more preferably 99.9 wt. % of the molecular sieves are in their hydrogen form.

The one or more molecular sieves used in the catalyst composition of the disclosure have a Si/Al atomic ratio ranging from 2 to 18, preferably from 5 to 18 or from 5 to 15. This can be obtained by performing a step of steaming the one or more molecular sieves before the contact of the catalyst composition with the feedstream, namely before step (c). The steaming step allows to adjust the Si/Al atomic ratio in the samples and sometimes to avoid using a very expensive organic template. Thus, the steaming step can be used to stabilize the catalyst composition.

Moreover, less aluminium also contributes to low coke formation and to low ageing rates. However, a certain amount of Al in the framework is important for the catalyst activity. Sometimes, the steaming could also eliminate the non-selective sites (non-paired sites). In this case, the sample subjected to the steaming could be preliminary exchanged with a bivalent cation ($Cu^{2+}$, $Co^{2+}$, $Ca^{2+}$, $Mg^{2+}$) followed by steaming and back ion-exchange to protons/ammonia forms.

Steaming can be performed at a temperature preferably comprised between 400° C. and 1000° C., more preferably comprised between 600° C. and 800° C. The steaming treatment is carried out in 10-95% steam inside a horizontal quartz tube oven, during a period ranging from 0.01 h to 200 h, preferably during a period ranging from 0.1 h to 24 h, at a steam pressure comprised between 0.1 bar to 10 bar. Afterwards, the samples were optionally dried in a nitrogen flow.

The catalyst subjected to steaming could be in powder or in shaped form.

Steaming, in addition to trigger aluminium leaching, also allows for the reduction of the number of acid sites.

In a preferred embodiment, the catalyst composition may contain one or more alkaline earth metal-containing materials. Said alkaline earth metal-containing material is selected from the group of beryllium, magnesium, calcium, strontium, barium, and any mixtures thereof.

In an embodiment, the catalyst composition further comprises from 1 to 50 wt. % of hydrotalcite as based on the total weight of the catalyst composition; preferably from 5 to 25 wt. %, more preferably from 7 to 23 wt. %, even more preferably from 10 to 20 wt. %.

In an embodiment, the one or more molecular sieves after or before steaming are doped with a phosphorus-containing material, so as to form a phosphate molecular sieve. The phosphate molecular sieve can be preferably further subjected to steaming. The catalyst composition can thus comprise between 0.1 wt. % and 7.0 wt. % of a phosphorus-containing material as based on the total weight of the catalyst composition, preferably between 0.3 wt. % and 4.5 wt. %, preferentially between 0.5 wt. % and 4.0 wt. %, more preferentially 2.0 wt. %.

The one or more molecular sieves can be doped with phosphorus-containing materials and with one or more alkaline earth metal-containing materials, preferably a magnesium or calcium-containing material. In this embodiment, the calcium and magnesium are strongly bound with phosphorous and less prone for the formation of bromides. However, the presence of the alkali earth metals on the initial molecular sieve is highly undesirable.

In one embodiment, the one or more molecular sieves are shaped with a binder, which is an inorganic material. The preferred binder is selected from silica, alpha-alumina, clays, alumina phosphates, calcium phosphates, magnesium phosphates, mullite. Preferentially, the binder is silica. The catalyst composition of the present disclosure preferably comprises at least 10 wt. % of a binder as based on the total weight of the catalyst composition. In an embodiment, the binder is present in an amount of at least 15 wt. % as based on the total weight of the catalyst composition; preferably, in an amount of at least 20 wt. %, most preferably in an amount of at least 30 wt. %, even more preferably in an amount of at least 40 wt. %, and most preferably in an amount of at least 50 wt. %. Typically, the catalyst composition of the present disclosure comprises between 15 wt. % and 35 wt. % of a binder as based on the total weight of the catalyst composition.

With preference, the one or more molecular sieves are transition metal-free and/or alkali metal-free.

Optional Modification of the Phosphorous Modified Steamed First Catalyst

The catalyst composition modified with a phosphorous containing-material may contain a metal-containing material, which is preferably an alkaline earth metal-containing material. However, the alkaline earth metal-containing material is spatially separated from the molecular sieve, in which alkaline earth metal is strongly bounded with phosphorous. The said alkaline earth metal is selected from the group of beryllium, magnesium, calcium, strontium, barium and any mixtures thereof.

The metal-containing material that can be added to a catalyst composition modified with phosphorous is advantageously in the form of alkaline earth metal salts and comprise at least one inorganic anion selected preferably from the group of oxides, silicates, aluminates, titanates, phosphates, borates and borosilicates. Suitable silicate anions include $SiO_3^{2-}$, $SiO_4^{4-}$, $Si_2O_7^{6-}$ and so on. Suitable borate anions include $BO_2^-$, $BO_3^{2-}$, $B_2O_5^{4-}$, $B_4O_7^{2-}$, $B_6O_{11}^{4-}$, $B_{10}O_{19}^{8-}$ and so on. Suitable aluminate anions include $Al_2O_4^{2-}$, $AlO_4^{5-}$, $Al_6O_{18}^{18-}$ and so on. Suitable titanate anions include $TiO_3^{2-}$, $Ti_3O_7^{2-}$, $Ti_4O_9^{2-}$, $TiO_4^{4-}$ and so on. Suitable phosphate anions include $PO_4^{3-}$, $HPO_4^{2-}$, $H_2PO_4^-$, $P_nO_{3n+1}^{(n+2)-}$ and so on. Bi-, tri- and poly-metal silicates, borates and borosilicates containing one, two or more alkaline earth metals selected from the list above can be used too. The metal salt may also comprise other anions.

Examples of suitable alkaline earth metal salts that can be added to a catalyst composition modified with phosphorous include $Mg_6Al_2CO_3(OH)_{16} \cdot 4(H_2O)$ (hydrotalcite), $Mg_2B_2O_5 \cdot H_2O$, $CaMgB_6O_{11} \cdot 6H_2O$ (hydroboracite), $Ca_2B_6O_{11} \cdot 5H_2O$ (colemanite), $Ca_4B_{10}O_{19} \cdot 7H_2O$, $Mg(BO_2) \cdot 8H_2O$, $Ca(BO_2) \cdot 2H_2O$, $BaB_6O_{10} \cdot 4H_2O$, $CaSi_6O_{17}(OH)_2$ (xonotlite), $CaMg(Si_2O_6)_x$, $Mg_2(Si_2O_6)_x$, $CaAl_2Si_2O_8$, $Mg_4Si_6O_{15}(OH)_2 \cdot 6H_2O$ (sepiolite), $(Mg,Al)_2Si_4O_{10}(OH) \cdot 4H_2O$ (palygorskite or attapulgite) and mixtures thereof.

A further example of suitable alkaline earth metals that can be added to a catalyst composition modified with phosphorous is $Mg(NO_3)_2$ (magnesium nitrate).

Before mixing with the molecular sieve, said alkaline earth metal salts may be modified by calcination, steaming, ion-exchange, impregnation, and/or phosphatation. Said alkaline earth metal salts may be an individual compound or may be a part of mixed compounds, for example, mixed with mineral, natural or chemical fertilizer.

In a preferred embodiment, the catalyst composition modified with phosphorous further comprises from 1 to 50 wt. % of hydrotalcite as based on the total weight of the catalyst composition; with preference from 5 to 25 wt. %, preferably from 7 to 23 wt. %, even more preferably from 10 to 20 wt. %. The hydrotalcite is of the formula $Mg_6Al_2CO_3(OH)_{16} \cdot 4(H_2O)$.

In another preferred embodiment, the one or more molecular sieves are doped with both at least one phosphorus-containing material and with at least one alkaline earth metal-containing material, preferably at least one magnesium-containing material and/or at least one calcium-containing material.

The Shaping of the First Catalyst with a Binder

According to the disclosure, one or more molecular sieves are shaped with a binder, which is an inorganic material, and preferentially silica. The molecular sieves shaped with the binder forms a catalyst composition, and the catalyst composition of the present disclosure preferably comprises at least 10 wt. % of a binder based on the total weight of the catalyst composition; with preference at least 50 wt. %.

In an embodiment, the binder is present in an amount of at least 15 wt. % as based on the total weight of the catalyst composition; preferably, in an amount of at least 20 wt. %, most preferably in an amount of at least 30 wt. %, even more preferably in an amount of at least 40 wt. %, and most preferably in an amount of at least 50 wt. %.

In one embodiment, the one or more molecular sieves are shaped with a binder, which is an inorganic material The preferred binder is selected from silica, alpha-alumina, clays, alumina phosphates, calcium phosphates, magnesium phosphates, mullite and any mixture thereof. Most preferentially, the binder is silica.

The binder preferably does not contain any aluminium compounds, such as alumina. This is because as mentioned above the preferred catalyst for use in the disclosure is de-aluminated by steaming to increase the Si/Al atomic ratio of the crystalline silicate. The presence of alumina in the binder, as well as the presence of hydrogen halides, may lead to the re-alumination of the molecular sieve. The presence of aluminium in the binder would also tend to reduce the olefins selectivity of the catalyst and to reduce the stability of the catalyst over time.

Non-limiting examples of silicon sources suitable for the binder of the catalyst composition include silicates, precipitated silicas, for example, Zeosil® available from Rhodia, fumed silicas, for example, Aerosil®200 available from Degussa Inc., New York, N.Y., silicon compounds such as tetraalkyl orthosilicates, for example, tetramethyl orthosilicate (TMOS) and tetraethylorthosilicate (TEOS), colloidal silicas or aqueous suspensions thereof, for example Ludox® HS-40 available from E.I. du Pont de Nemours, Wilmington, Del., silicic acid, alkali-metal silicate, or any combination thereof.

Other suitable forms of amorphous silica include silica powders, such as Ultrasil® VN3 SP (commercially available from Degussa).

Other non-limiting examples of a suitable solid silica source are special granulated hydrophilic fumed silicas, mesoporous silica and high surface area precipitated silica SIPERNAT® from Evonik, Hi-Sil 233 EP (available from PPG Industries) and Tokusil (available from Tokuyama Asia Pacific).

In addition, suitable amorphous silica sources include silica sols, which are stable colloidal dispersions of amorphous silica particles in an aqueous or organic liquid medium, preferably water.

Non-limiting examples of commercially available silica sols include those sold under the tradenames Nyacol® (available from Nyacol Nano Technologies, Inc. or PQ Corp.), Nalco (available from Nalco Chemical Company), Ultra-Sol (available from RESI Inc), Ludox® (available from W.R. Grace Davison), NexSil™ (available from NNTI).

Many silica sols are prepared from sodium silicate and inevitably contain sodium. It is, however, found that the presence of sodium ions can cause sintering of the silica body at high temperature and/or affect catalytic performance. Therefore, if silica sols containing sodium are used, a step of ion exchange may be required in order to reduce or remove sodium. To avoid carrying out ion exchange steps, it is convenient to use silica sols that contain very little or, ideally, no detectable traces of sodium and have a pH value of less than 7. Most preferably, the silica sol used in the process is slightly acidic with or without polymeric stabilizers. Non-limiting examples of silica sols that contain no detectable traces of sodium include Bindzil® 2034DI, Levasil® 200, Nalco 1034A, Ultra-Sol 7H or NexSil™ 20A.

In some case, silica dispersion prepared with alkylammonium might be useful. Non-limiting examples of commercially low sodium silica sols stabilized by ammonia or alkylammonium cations include LUDOX® TMA (available from W.R. Grace Davison) or VP WR 8520 from Evonik.

The silica sols with higher $SiO_2$ content than 30 wt. % and even up to 50 wt. %, for example, W1250, W1836, WK341, WK7330 from Evonik are particularly preferred.

The preferred source of silicon is a silica sol or a combination of silica sol with precipitated or fumed silica.

In an embodiment, the binder is present in an amount of at least 10 wt. % as based on the total weight of the catalyst composition; preferably, in an amount of at least 20 wt. %, most preferably in an amount of 30 wt. %, even more preferably in an amount of at least 40 wt. %, and most preferably in an amount of at least 50 wt. %.

The Second Catalyst Composition

The second catalyst composition is a catalyst suitable for an olefin cracking reaction. Preferred catalysts for the olefin cracking reaction can be selected from one or more molecular sieves and/or one or more clays.

The one or more molecular sieves are selected from one or more silico aluminophosphates and/or one or more zeolites, preferably the one or more molecular sieves are one or more zeolites.

With preference, said cracking catalyst comprises one or more molecular sieves selected from silicalites from the MFI family, crystalline silicate from the MFI family with a Si/Al atomic ratio of at least 180, crystalline silicate from the MEL family with a Si/Al atomic ratio ranging between 150 and 800, and/or phosphorous-modified molecular sieve from the MFI, MEL, FER, MOR family and/or phosphorous-modified clinoptilolite.

In one embodiment, said cracking catalyst comprises one or more molecular sieves selected from silicalites from the MFI family, optionally with a silica binder.

Examples of suitable catalysts were disclosed in the international patent application published WO2004/048299.

Examples of crystalline silicate from the MFI family are ZSM-5 and silicalite. An example of crystalline silicate from the MEL family is ZSM-11, which is known in the art. Other suitable non-limiting examples are boralite D and silicalite-2, or any mixtures thereof.

The preferred crystalline silicates have pores or channels defined by ten oxygen rings and a high Si/Al atomic ratio. The catalyst having a high Si/Al atomic ratio may be manufactured by removing aluminium from a commercially available catalyst. The commercially available catalysts may be modified by steaming to remove at least part of inter-framework aluminium followed by leaching step to remove external aluminium.

The cracking catalyst can be formulated with a binder, preferably an inorganic binder, and shaped to a desired shape, e.g. extruded pellets. The binder is an inorganic material selected from clays, silica, metal oxides. Preferably, the binder content ranges from 5 to 50% by weight, more typically from 15 to 35% by weight, based on the weight of the cracking catalyst. More preferably, the binder is a silica binder.

The cracking catalyst can be subjected to a steaming step before step (d).

The olefin cracking reaction is known per se. It has been described in EP1035915, EP1036133, EP1036134, EP1036135, EP1036136, EP1036137, EP1036138, EP1036139, EP1190015, EP1194500, EP1194502, and EP1363983. The content of which is incorporated in the present description.

The Process of the Disclosure

When the catalysts are ready, the first catalyst composition is filled in a first reaction zone and the second catalyst composition is filled in a second reaction zone, the first reaction zone being upstream of the second reaction zone. The two reaction zones can be two separate reactors fluidly connected together or two separate part of one single reactor. Said separate reactors or said single reactor can be a fixed bed, a fluidized bed or another suitable reactor. Preferentially it can be a fixed-bed tubular reactor. In this case, the diameter of the inner tube may be of 11 mm.

With preference, the catalyst is pre-activated before the step of contacting the feed. The pre-activation is actually a step of calcination and is performed at high temperature, preferably between 500° C. and 550° C. The molecular sieve is preferably calcinated for at least 5 hours, preferentially for at least 6 hours. The molecular sieve is calcinated before the step of contacting in a nitrogen atmosphere. The step of calcination provides for a crystalline structure to the molecular sieve.

The process comprises the step of providing a feedstream to be contacted by the catalyst, the feedstream comprises one or more methyl halides; optionally, diluted in at least one diluent. Said diluent can be one or more of gaseous nitrogen, $H_2$, hydrogen halides, $CO_2$, steam, monocyclic aromatics (e.g. benzene, toluene, and/or xylene), non-converted $CH_4$, CO, $C_2H_6$, $C_3H_8$, $C_4H_{10}$.

The temperature below 400° C., preferentially below 390° C., more preferentially below 380° C., is important to limit the thermal decomposition of the one or more methyl halides, especially methyl bromide. This is less important for methyl chloride (used often in the prior art), which is more thermally stable.

In the same time, methyl bromide is much more reactive and its transformation at lower reaction temperature on the materials according to the disclosure occurs substantially via a different to hydrocarbon pool mechanism and leads to the formation of non-cyclic C3-C6 olefins with a limited amount of ethylene and coke. The catalyst performance is stable and allows to implement the catalysts in cheaper reactor technology. For these reasons, it is preferred that the reaction conditions include a reaction temperature ranging from 220° C. to 390° C.; more preferably ranging from 280° C. to 380° C. In general, higher temperatures favour the conversion.

In a preferred embodiment, the feedstream contains less than 500 ppm of water and water precursor compounds such as alcohols, aldehydes, and/or carboxylic acids.

The molar ratio diluent/methyl halide is ranging between 2 and 20, preferentially between 3 and 10. A highly diluted feedstream favours a high level of conversion while a weakly diluted feedstream favours the selectivity towards the formation of C3-C6 olefins.

In a preferred embodiment, the halogen of said one or more methyl halides is F, Cl, Br, or I, preferentially Br.

The methyl halide comprised in the feedstream can optionally comprise 1, 2, 3 or 4 halogens. Advantageously, the methyl halide comprised in the feedstream comprises 1 halogen and is a monohalo-methyl. In this case, it is advantageous that the halide is a bromide.

The one or more methyl halides optionally comprise up to 10 wt. % of methyl dihalide.

With preference, the weight of feed flowing per unit of weight of the catalyst per hour (weight hourly space velocity, WHSV) is comprised between 0.1 $h^{-1}$ and 100 $h^{-1}$, preferentially comprised between 1.0 $h^{-1}$ and 15 $h^{-1}$. More preferably, WHSV is comprised between 1.5 $h^{-1}$ and 10 $h^{-1}$. Even more preferably, WHSV is comprised between 2.0 $h^{-1}$ and 6.0 h$^{-1}$. This means that the catalyst of the present disclosure is able to convert a weight of the feed that is superior to the amount of the catalyst present in the reactor.

Preferably, the reaction conditions of step (c) include a pressure ranging from 0.1 MPa to 2 MPa, preferably ranging from 0.2 to 1 MPa.

A first product stream is obtained. The first product stream is an effluent comprising C3-C6 olefins, hydrogen halide, unreacted one or more methyl halides, alkane and higher hydrocarbons and optionally said diluent. The selectivity to C3-C6 olefin is of at least 70%, preferentially of at least 75%.

In a preferred embodiment, the hydrogen halides are removed from said first product stream before the cracking step, preferentially by gas purification techniques, by directing said first product stream through a wet scrubber (e.g. water scrubber or a water stripper) through an acetic acid extractive distillation vessel, or by an oxidation unit that contains preferentially a metal oxide reactor bed. In another preferred embodiment, the unreacted one or more methyl halides are recovered before the cracking step, preferentially by distillation of the first product stream. The unreacted one or more methyl halides can be preferentially reinjected said into the feedstream of step (a). In yet another preferred embodiment, the aromatics are removed from said first product stream before the cracking step, preferentially by distillation of the first product stream. These purification steps promote the cracking step since the potential impurities (hydrogen halide, unreacted methyl halide and/or aromatics) that could prevent the good functioning of the cracking step are removed.

In a preferred embodiment, at least part of C2 hydrocarbons separated from the first product stream or from the second product stream and could be reinjected into said feedstream of step (a).

In a preferred embodiment, at least part of C4 hydrocarbons could be separated from the first product stream or from the second product stream and could be reinjected into said feedstream of step (a).

The first product stream is then contacted with the second catalyst composition under second reaction conditions.

With preference, in the second vessel or in the second reactor, the weight of feed comprising flowing per unit of weight of the catalyst per hour (weight hourly space velocity, WHSV) is comprised between 0.1 h$^{-1}$ and 100 h$^{-1}$, preferentially between 1.0 h$^{-1}$ and 15 h$^{-1}$. More preferably, WHSV is comprised between 1.5 h$^{-1}$ and 10 h$^{-1}$. Even more preferably, WHSV is superior than 1 h$^{-1}$ but lower or equal to 100 h$^{-1}$. This means that the second catalyst of the present disclosure is able to convert a weight of the feed that is superior to the amount of the second catalyst present in the second reactor.

In a preferred embodiment, the second reaction conditions of step (d) include a reaction temperature ranging from 500° C. to 600° C.; preferably ranging from 510° C. to 590° C.; more preferably ranging from 520° C. to 580° C.

Preferably, the second reaction conditions of step (d) include a pressure ranging from 10 kPa to 500 kPa, preferably ranging from 20 kPa to 300 kPa.

A second product stream is thus obtained. The second product stream is an effluent comprising mainly ethylene and propylene. One or more side products may be produced as well, such as methane, ethane, propane, C4+ olefins, C5+ linear hydrocarbons and BTX). In a preferred embodiment, at least part of said second product stream could be recycled back to the cracking reactor of step (d).

In an embodiment, the step (d) of contacting the first product stream with the second catalyst composition is followed by a step (e) of performing a separation of ethylene and propylene from the second product stream. The step (e) may be preferentially carried out by performing at least one compression and/or at least one distillation of said second product stream.

In a preferred embodiment, the aromatics are removed from said second product stream before the recycling.

Figure 2:
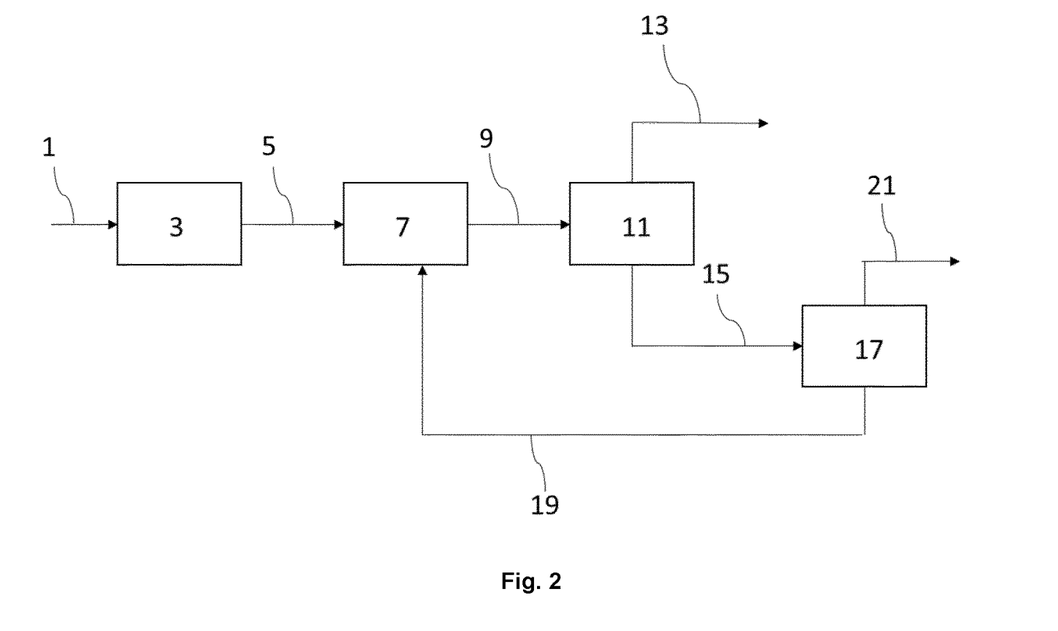
FIG. 2 shows a first possible implementation of the process of the present disclosure.
Figure 3:
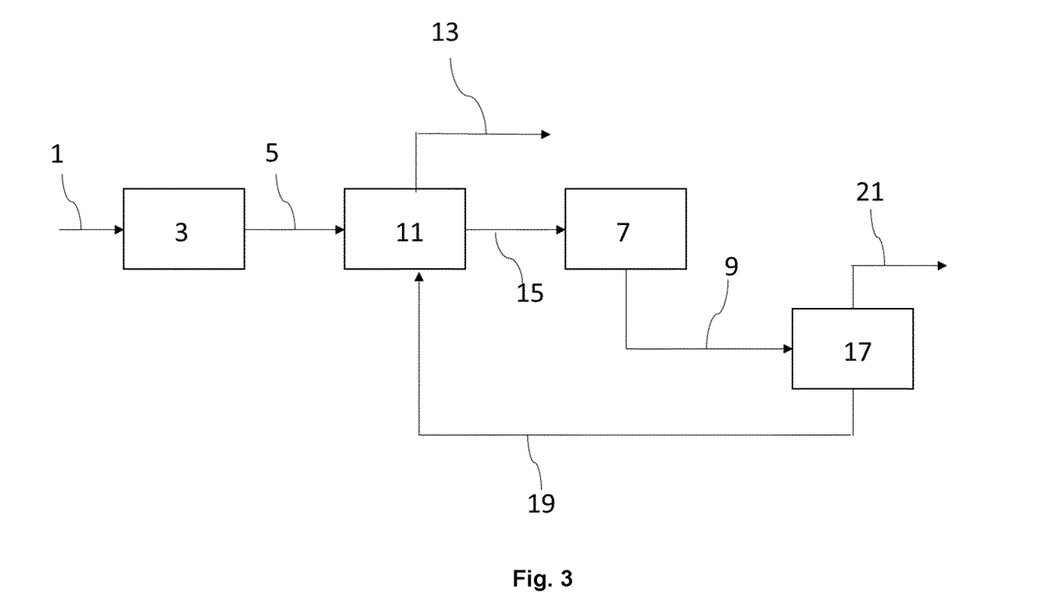
FIG. 3 shows a second possible implementation of the process of the present disclosure.
Figure 4:
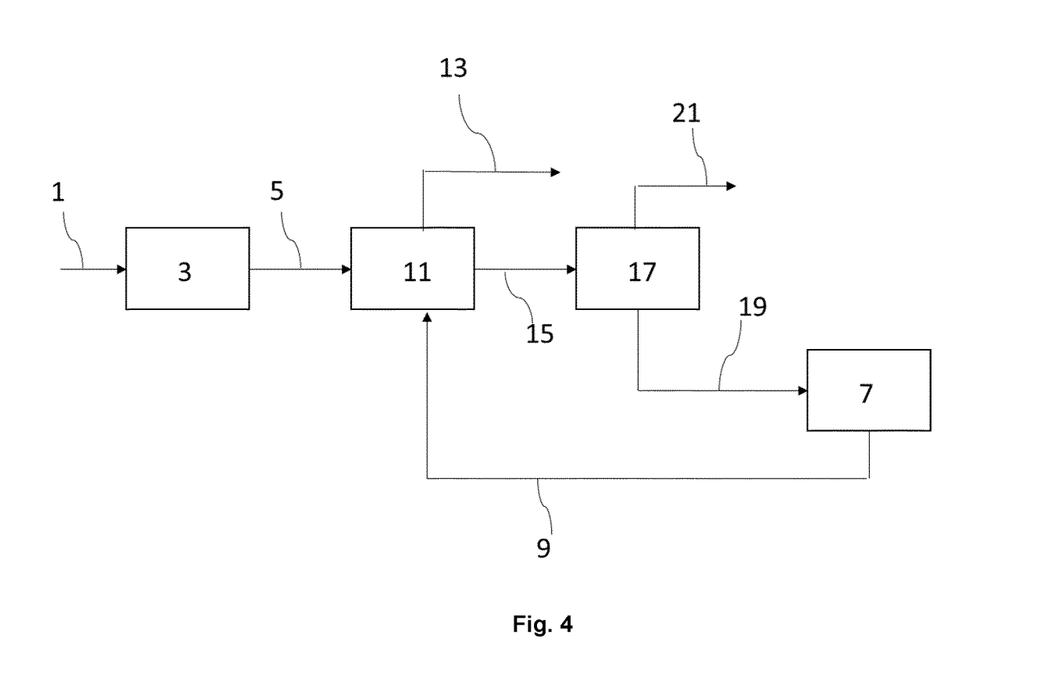
FIG. 4 shows a third possible implementation of the process of the present disclosure.

The FIGS. 2, 3 and 4 depict some of the possible implementations of the process of the disclosure:

A feedstream 1 comprising methyl bromide as methyl halides and hydrogen bromide as diluent is introduced into the first reaction zone 3. The first catalyst composition in the first reaction zone 3 converts said feedstream 1 into a first product stream 5 comprising C2-C9 hydrocarbons (with a selectivity of at least 70% into acyclic C3-C6 olefins), and also methane. The first product stream 5 also comprises hydrogen bromide and unreacted methyl bromide.

As shown in FIG. 2, the first product stream 5 can be directed in totality through the second reaction zone 7, so as to produce a second product stream 9 that is then treated in a separation unit 11, for example, a compression or an extractive distillation unit. This treatment in the separation unit 11 affords a stream 13, comprising essentially ethylene and propylene, and a C4+ stream 15 that can be further passed through an additional separation unit 17, preferably a deoctanizer. From said additional separation unit 17, the high boiling point fraction 21, preferably comprising C8+ compounds, is recovered and can be valorised as fuel. The low boiling point fraction 19, comprising C4-C7 compounds, is also recovered and recycled to the second reaction zone 7.

Alternatively, as shown in FIG. 3, the first product stream 5 is directed in a separation unit 11, to afford a C4+ stream 15 which is then directed in the second reaction zone 7. The second product stream 9 is then treated through an additional separation unit 17, which allows to recover a low boiling point fraction 19 comprising essentially ethylene and propylene but also C4-C7 compounds. The low boiling point fraction 19 is redirected through the separation unit 11, which allows for the separation of the stream 13 comprising essentially ethylene and propylene. In this implementation, the C4-C7 compounds of the low boiling point fraction 19 can also be recycled.

Alternatively yet, and as shown in FIG. 4, the first product stream 5 is directed in a separation unit 11, to afford a C4+ stream 15 which is then directed through an additional separation unit 17, preferably a deoctanizer. This allows for removing a high boiling point fraction 21, preferably comprising C8+ compounds, that can be valorised as fuel, and to allow the low boiling point fraction 19, comprising essentially C4-C7 compounds, to go through the second reaction zone 7 in order to be subjected to the cracking step. The second product stream 9 generated from said second reaction zone 7, which comprises essentially ethylene and propylene, but also C4+ compounds, is then redirected to the separation unit 11 which allows for the separation of the stream 13 comprising essentially ethylene and propylene. With this configuration, the C4+ compounds are thus separated from the second product stream 9 and can be recycled.

Test and Determination Methods

The conversion of the monohalo-methyl ($X_{CH_yX}$) is determined according to formula (1):

$$X_{CH_3X} = \frac{[CH_3X]^i - [CH_3X]^f}{[CH_3X]^i} \times 100 \quad (1)$$

wherein $[CH_3X]^i$ and $[CH_3X]^f$ are the molar concentration of the monohalo-methyl $CH_3X$ in the (initial) feed and in the (final) effluent (or product stream) respectively.

The selectivity in methane (C1) is determined according to formula (2):

$$S_{methane} = \frac{[CH_4]}{[CH_4] + 2[C_2H_4] + 2[C_2H_6] + 3[C_3H_6] + 3[C_3H_8] + 4[C_4H_8] + 4[C_4H_{10}] + \ldots} \times 100 \quad (2)$$

wherein the numerator is the carbon adjusted molar concentration of methane and the denominator is the sum of all the carbon adjusted molar concentration of all hydrocarbon in the effluent.

The selectivity in ethylene (C2=) is determined according to formula (3):

$$S_{ethylene} = \frac{2[C_2H_4]}{[CH_4] + 2[C_2H_4] + 2[C_2H_6] + 3[C_3H_6] + 3[C_3H_8] + 4[C_4H_8] + 4[C_4H_{10}] + \ldots} \times 100 \quad (3)$$

wherein the numerator is the carbon adjusted molar concentration of ethylene and the denominator is the sum of all the carbon adjusted molar concentration of all hydrocarbon in the effluent.

The selectivity in propylene (C3=) is determined according to formula (4):

$$S_{propylene} = \frac{3[C_3H_6]}{[CH_4] + 2[C_2H_4] + 2[C_2H_6] + 3[C_3H_6] + 3[C_3H_8] + 4[C_4H_8] + 4[C_4H_{10}] + \ldots} \times 100 \quad (4)$$

wherein the numerator is the carbon adjusted molar concentration of propylene and the denominator is the sum of all the carbon adjusted molar concentration of all hydrocarbon in the effluent.

Similar equations (not shown) are used for determining the selectivity in butylene, pentene, hexene and heptane, and also for the corresponding alkanes.

The selectivity in aromatics is determined according to formula (5):

$$S_{aromatics} = \frac{6[C_6H_6] + 7[C_7H_8] + 8[C_8H_{10}]}{[CH_4] + 2[C_2H_4] + 2[C_2H_6] + 3[C_3H_6] + 3[C_3H_8] + 4[C_4H_8] + 4[C_4H_{10}] + \ldots} \times 100 \quad (5)$$

wherein the numerator is the carbon adjusted molar concentration of aromatics (benzene, toluene and xylene) and the denominator is the sum of all the carbon adjusted molar concentration of all hydrocarbon in the effluent.

Gas chromatography was performed on Columns: DB1 (40 m, 0.1 mm, 0.4 µm) and $Al_2O_3$ (50 m, 0.32 mm, 5 µm) using Agilent operated by ChemStation software.

The metal content was determined by X-ray fluorescence (XRF) spectroscopy using an Orbis Micro-EDXRF spectrometer equipped with a Rh source (15 kV, 500 µA) and a silicon drift detector.

The Si/Al atomic ratio corresponds to the amount of $SiO_2$ divided by the amount of $Al_2O_3$ taking into account the fact there are two atoms of aluminium for one atom of silicon. The silica to alumina ratio (also stated as SAR) corresponds to the amount of $SiO_2$ divided by the amount of $Al_2O_3$ notwithstanding the proportion of the Si atoms over the Al atoms in the chemical formula of the molecular sieve. Therefore, the value of the SAR always corresponds to twice the value of the Si/Al atomic ratio.

Si/Al Atomic Ratio in Molecular Sieve by X-Ray Fluorescence (XRF) and Magic Angle Spinning Nuclear Magnetic Resonance (MAS NMR) of Aluminium.

The Si/Al atomic ratio in molecular sieve could be determined by a combination of the XRF elemental analysis and $^{27}Al$ MAS NMR. The $^{27}Al$ MAS NMR is useful to determine which fraction of the alumina is in the extra framework position.

Prior to the acquisition of $^{27}Al$ MAS spectra, the samples were hydrated in 100% relative humidity (RH) in a closed vessel filled with pure water for 24 hours (at least) to equilibrate the molecular sieve structure (a symbol H is added at the end of the number). This procedure allows reconstructing the missing OH groups (missing bonds, loose coordination of Al) thus diminishing the quadrupolar constant of $^{27}Al$. Finally, the quantity of non-observable $^{27}Al$ by NMR is reduced. The 15 kHz $^{27}Al$ magic angle spinning (MAS) NMR spectra were registered on Bruker Avance III HD 500 MHz (the magnetic field is 11.7 T) equipment by means of the broadband MAS probe using 4 mm outer diameter rotors at the spinning speed of 15 kHz (operating frequency is 130.31 MHz). The pulse sequence contained one single excitation pulse of 0.5 µs ($\pi/8$) duration (pulse nutation frequency 54.3 kHz), the interpulse delay was 0.5 s, the number of transients was 4096.

Figure 5:
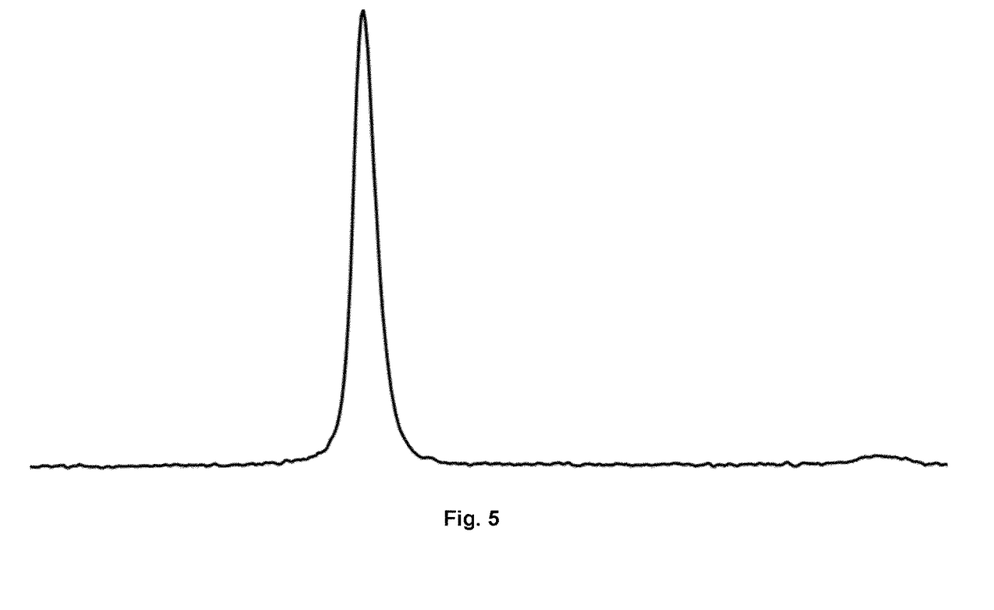
FIG. 5 shows the $^{27}$Al MAS spectrum of SSZ-13, which is equivalent to the $^{27}$Al MAS spectrum of SSZ-39.

FIG. 5 shows the $^{27}Al$ MAS spectrum of SSZ-13, which is equivalent to the $^{27}Al$ MAS spectrum of SSZ-39. The signal at 55-60 ppm corresponds to the framework of tetrahedrally coordinated Al. As there are no signals visible at 0 ppm, it means that there is not extra-framework aluminium. With this information, by performing elemental analysis with X-Ray fluorescence (XRF) experiments, it is thus possible to determine the Si/Al atomic ratio of the molecular sieve framework $(Si/Al)_{fr}$.

$$(Si/Al)_{fr} = (Si/Al) \text{ elemental analysis} \times (I_{57} + I_0)/I_{57} \quad (6)$$

wherein
(Si/Al) elemental analysis is the ratio of the content of Si and of the content of Al as determined by XRF;
$I_{57}$ is the $^{27}Al$ MAS NMR peak intensity at $\delta$ of 57 ppm; and
$I_0$ is the $^{27}Al$ MAS NMR peak intensity at $\delta$ of 0 ppm.

In this case, as there is no extra-framework aluminium, the Si/Al atomic ratio of the molecular sieve corresponds to the data obtained from the elemental analysis.

The sample for the XRF is under the form of pearl, obtained from a calcined molecular sieve. The calcination temperature for the XRF experiments is 900° C. A correction based on LOI (Loss Of Ignition) has been performed to remove any volatile compounds that might interfere with the determination of elemental analysis of the sample. AXIOS instrument has been used to measure the content of Si and Al by XRF.

Figure 6:
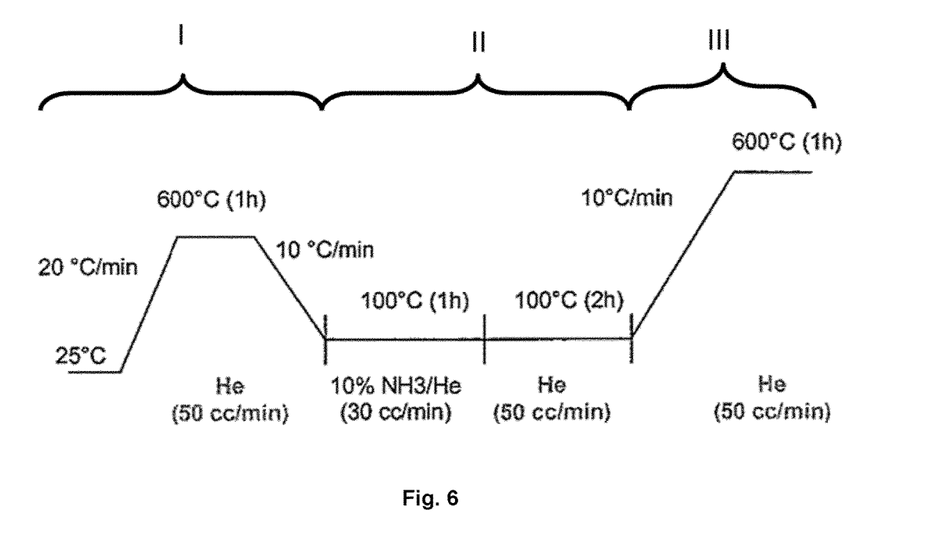
FIG. 6 shows an example of the settings of the temperature-programmed desorption (TPD) method.

Temperature Programmed Desorption (TPD) is the method of observing desorbed molecules from a surface when the surface temperature is increased. It has been performed by following the heating sequences I, II and III shows on FIG. 6, respectively corresponding to activation, saturation and analysis. In brief, in the first step (marked as I on FIG. 6), starting from room temperature (25° C.) under a flow of helium (rate 50 cc/min), the temperature has been gradually increased to 600° C. at a rate of 20° C./min. After 1 hour at 600° C., the molecular sieve sample is considered as being activated and the temperature is then gradually decreased to 100° C. at a rate of 10° C./min. Then, in the second step (marked as II on FIG. 6) during 3 hours, the temperature is maintained at 100° C. and in the first 1 hour, 10% of ammonia ($NH_3$) is added to the helium flow (which is decreased to 30 cc/min). The surface of the molecular sieve is thus saturated with the molecules of ammonia that are going to be adsorbed onto the surface. The last 2 hours of the temperature threshold at 100° C., the initial flow of helium is reinstated. Then, in the third step (marked as III in FIG. 6) the temperature is increased again to 600° C. at a rate of 10° C./min in order to desorb the ammonia. The sample is maintained at 600° C. for an additional one hour. It is highlighted that the skilled person could use different parameters (time, temperature, flow rate, carrier gas) to perform the method. The measurement of the amount of ammonia using a thermal conductivity detector allows to recognize the different adsorption conditions of the ammonia onto the molecular sieve and allows for obtaining a description of the surface of the molecular sieve, such as the number of acid sites.

EXAMPLES

The embodiments of the present disclosure will be better understood by looking at the different examples below.

Examples 1 to 3 concern step (c) of the process according to the disclosure.

Example 4 is an example showing the results of the additional step of cracking, corresponding to step (d) of the process of the present disclosure.

Example 1A: A catalyst composition comprising steamed SSZ-39 molecular sieve having Si/Al atomic ratio of 10 (no extra framework Al) was prepared. SSZ-39 molecular sieve was steamed to form a molecular sieve having Si/Al atomic ratio of 10 (SAR of 20).

Example 1B: A catalyst composition comprising steamed SSZ-13 molecular sieve having Si/Al atomic ratio of 2.8 (no extra framework Al) was prepared. SSZ-13 molecular sieve was steamed to form a molecular sieve having Si/Al atomic ratio of 2.8 (SAR of 5.6).

Each catalyst composition was used as a catalyst for $CH_3Br$ conversion in a fixed-bed tubular reactor at a temperature of 340° C. for a period of 48 h or longer. For the catalytic test, the powder was pressed, then crushed and seized between 35-45 mesh screens. In the test, a fresh load of the seized catalyst of 10 mL (i.e. 6.3 g) was loaded in a reactor (11 mm inner diameter) and the catalyst was preactivated in an $N_2$ flow at 525° C. for 6 h. Then, the temperature was decreased to 340° C. and pure $N_2$ flow was replaced with the flow of $N_2/CH_3Br$ 10/1 mol. with WHSV of $CH_3Br$/catalyst of 1.6 $h^{-1}$. The reactor pressure was 2 barA during the test run. (2 barA means that there is a difference of 2 bar ($2.10^5$ Pa) relative to the absolute vacuum).

The results are reported in table 1 and compared to prior art results given in US2017/0057886.

TABLE 1

Conversion and selectivity results: example 1 vs. prior art

| Catalyst | Example 1A | Example 1B | Comparative Example 1[1] |
|---|---|---|---|

TABLE 1-continued

Conversion and selectivity results: example 1 vs. prior art

| Catalyst | SSZ-39 | SSZ-13 | SSZ-13 |
|---|---|---|---|
| SAR | 20[†] | 5.6 | 40 |
| Si/Al atomic ratio | 10 | 2.8 | 20 |
| Temperature (° C.) | 340 | 340 | 450 |
| Pressure | 3 barA | 3 barA | 1 barA |
| Partial pressure of $CH_3X$ | 0.30 | 0.30 | 0.25 |
| WHSV ($h^{-1}$) | 1.6 | 1.6 | 0.8-3.0 |
| $N_2/CH_3Br$ (mol/mol) | 10/1 | 10/1 | — |
| $N_2/CH_3Cl$ (mol/mol) | — | — | 4/1 |

| Product | Selectivity (%) | | |
|---|---|---|---|
| methane | <0.05 | <0.05 | n.d. |
| ethane | <0.01 | <0.01 | <2 |
| C3 | 0.6 | 0.7 | |
| C4 | 1.6 | 0.4 | |
| C5 | <0.05 | 0.2 | 0 |
| C6 paraffins | <0.01 | <0.01 | 0 |
| C6 = | 12.6 | 8.8 | 0 |
| C5 = | 22.9 | 11.3 | |
| C4 = | 10.8 | 9.8 | <15 |
| C3 = (propylene) | 32.8 | 44.3 | 33.99 |
| C7+ unsaturated hydrocarbons | 9.9 | 1.6 | 0 |
| Bromides | 0.6 | 2.4 | n.d. |
| Aromatics | 2.5 | <0.01 | <1 |
| C2 = (ethylene) | 5.6 | 20.5 | 34.95 |
| C3 =/C2 = ratio | 5.86 | 2.16 | 0.97 |
| Total selectivity to C3-C6 olefins | 79.1 | 74.2 | <48.99[(2)] |
| Total selectivity to alkanes | <2.36 | <1.4 | <2 |
| Conversion | 50 | 30 | 98.93 |
| Stability | >24 hours | >24 hours | <1 hour |

[†] as defined from X-Ray Fluorescence (XRF) and $^{27}Al$ MAS NMR; or from Si/Al elemental analysis and $^{29}Si$ MAS NMR
[(1)] Comparative Example 1 corresponds to example B of US2017/0057886.
[(2)] data for C3-C4 olefins only, since higher compounds are not generated.

From the results, it can be seen that the molecular sieve catalyst SSZ-39 from the AEI family and the molecular sieve catalyst SSZ-13 from the CHA family, both having a plurality of pores with a shape of 8-membered ring or less and the process of the disclosure achieve a high selectivity to C3-C6 olefins (79.1% and 74.2%, respectively) whereas, in the prior art, no production of higher olefins was observed, leading to a significant drop in the production of C3-C6 olefins (less than 49%). Moreover, it was possible to restrain the generation of ethylene, as demonstrated by the propylene/ethylene molar ratio (C3=/C2= ratio) which is superior to 1 in examples 1A and 1B, while said ratio is inferior to 1 in the comparative example.

As the bond C—Br in $CH_3Br$ is weak, due to the softness of the bromine atom, it is possible to convert $CH_3Br$ into hydrocarbons on a catalyst at lower temperature than the one know in the art. Indeed, at temperature superior than 420° C., olefin cracking might already take place (without providing another catalyst composition as in the present disclosure), which would increase the yield of ethylene and subsequently decrease the total selectivity to C3-C6 olefins (see comparative example 1). However, at much lower operating temperature, namely at a temperature below 400° C., examples 1A and 1B have demonstrated that a higher C3=/C2= molar ratio is enabled. The lower temperatures further allow to maintain the stability of the catalysts, for period over 24 hours.

Examples 2 and 3 and Comparison with Example 1A

Example 2 was conducted using the same conditions as in example 1A, except that the velocity was increased from 1.6 h$^{-1}$ to 5.0 h$^{-1}$ and the flow of methyl bromide was increased, the ratio N$_2$/CH$_3$Br changing from 10/1 to 10/3.

Example 3 was conducted using the same condition as in example 2, except that the temperature was decreased from 340° C. to 280° C.

Table 2 reports the results in accordance with the three examples of the disclosure.

TABLE 2

Conversion and selectivity results: examples 1 to 3

| Catalyst | Example 1A | Example 2 SSZ-39 | Example 3 |
|---|---|---|---|
| SAR† | 20 | 20 | 20 |
| Si/Al atomic ratio | 10 | 10 | 10 |
| Temperature (°C) | 340 | 340 | 280 |
| Pressure (barA) | 3 | 3 | 3 |
| WHSV (h$^{-1}$) | 1.6 | 5 | 5 |
| N$_2$/CH$_3$Br (mol/mol) | 10/1 | 10/3 | 10/3 |
| Product | Selectivity (%) | | |
| methane | <0.05 | <0.05 | <0.1 |
| ethane | <0.05 | <0.05 | <0.1 |
| C3 | 0.6 | 1.4 | 4.0 |
| C4 | 1.6 | 3.1 | 6.4 |
| C5 | <0.05 | 0.2 | 1.0 |
| C6 paraffins | <0.01 | 0.1 | 0.2 |
| Total selectivity to alkane | <2.36 | <4.9 | <11.8 |
| ethylene | 5.6 | 3.6 | 0.9 |
| C3 = (propylene) | 32.8 | 30.0 | 16.6 |
| C4 = | 10.8 | 14.3 | 15.6 |
| C5 = | 22.9 | 21.4 | 28.6 |
| C6 = | 12.6 | 19.8 | 15.6 |
| C7+ unsaturated hydrocarbons | 9.9 | 3.2 | 7.7 |
| Total selectivity to C3-C6 olefins | 79.1 | 85.5 | 76.4 |
| Aromatics | 2.5 | 1.8 | 2.7 |
| Bromides | 0.6 | 0.9 | 0.7 |
| Conversion | 50 | 15 | 8 |

†as defined from X-Ray Fluorescence (XRF) and $^{27}$Al MAS NMR; or from Si/Al elemental analysis and $^{29}$Si MAS NMR From the results, it can be seen that the increase of flow of methyl bromide allows for a better selectivity to C3-C6 olefins (85.5% instead of 79.1%). Additionally, the production of ethylene drops from 5.6% to 3.6%. By further applying a lower temperature, the quantity of ethylene can even be reduced to less than 1%, while a still elevated total selectivity to C3-C6 olefins is obtained (76.4%).

Those selectivity results are however counterbalanced by a decrease into the conversion.

Example 4

A catalyst composition comprising steamed and acidified ZSM-5 to form a silicalite from the MFI family having a Si/Al ratio of 1000 with SiO$_2$ binder was prepared.

Figure 7:
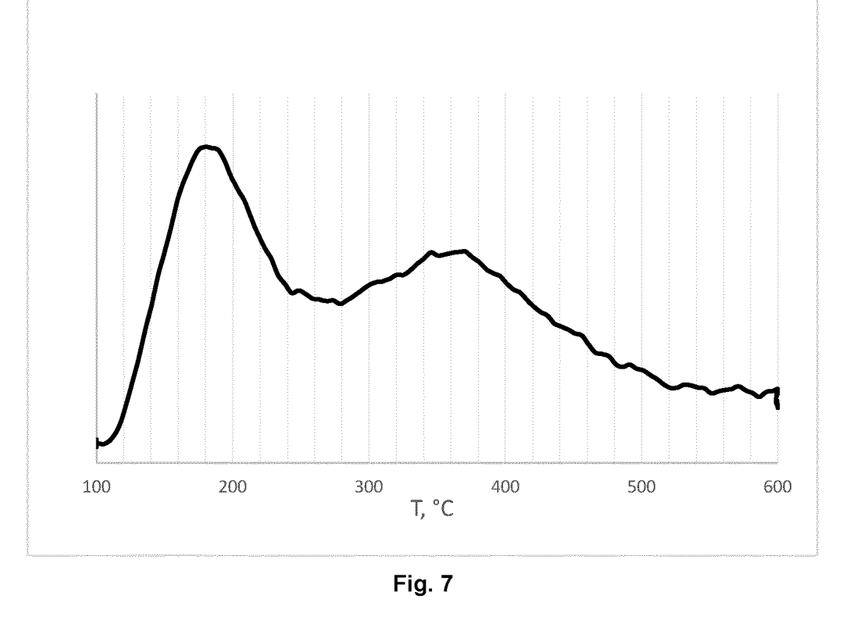
FIG. 7 shows the NH$_3$-TPD profile of the catalyst of the second catalyst composition according to the disclosure.

The particulars of said catalyst composition, as determined by the TPD (Temperature Programmed Desorption) test, show that the acid site density (μmol/g-cat), measured from the amount of NH$_3$ desorbed, is of 32 μmol/g-cat for the first peak and 49 μmol/g-cat for the second peak (see FIG. 7). Therefore, the Brønsted acid sites are present in a concentration of 81 μmol/g-cat.

ZSM-5 aluminosilicate was steamed and acidified to form a silicalite from the MFI family having a Si/Al ratio of 1000. With a SiO$_2$ binder, said catalyst composition has been used in the cracking step of the first product stream originating from example 1.

The cracking reactor was operating at a temperature of 550° C. with a weight hourly space velocity of 10 h$^{-1}$ and at a pressure of about 0.7 MPa. Table 3 indicates the results of the cracking step.

TABLE 3

Result of example 4

| Catalyst | Example 4 silicalite# with SiO$_2$ binder |
|---|---|
| SAR | >200† |
| Si/Al atomic ratio | >100 |
| Temperature (° C.) | 550 |
| Pressure | 0.7 MPa |
| WHSV (h$^{-1}$) | 10 |
| Product | Selectivity (%) |
| methane | 0.6 |
| ethane | 0.7 |
| C3 | 1.9 |
| C4 | 2.0 |
| C5 | 1.1 |
| C6 paraffins | 0.3 |
| Total selectivity of alkane | 7.0 |
| C2 = (ethylene) | 13.9 |
| C3 = (propylene) | 62.4 |
| C4 = | <0.01 |
| C5 = | <0.01 |
| C6 = | <0.01 |
| Aromatics | 5.3 |
| Bromides | 0.6 |
| Conversion | >99 |
| Yield of ethylene and propylene | >75 |

†as defined from TPD measurement.

Using the process of the present disclosure, it was thus possible to obtain a yield of ethylene and propylene from methyl bromide as starting material of at least 75%.

The invention claimed is:

1. Process for converting one or more methyl halides to ethylene and propylene, said process comprising the following steps:
   a) providing a feedstream (1) comprising one or more methyl halides; optionally, diluted in at least one diluent;
   b) providing a first catalyst composition and a second catalyst composition, said second catalyst composition comprising a cracking catalyst;
   c) contacting said feedstream (1) with said first catalyst composition in a first reaction zone (3) under first reaction conditions to provide a first product stream (5); and
   d) subjecting at least a part of said first product stream (5) to an olefin catalytic cracking with said second catalyst composition in a second reaction zone (7) under second reaction conditions to provide a second product steam (9),
   the process is characterized in that
   said first reaction conditions include a reaction temperature below 400° C., and in that said first catalyst composition comprises a first catalyst composition molecular sieve with a Si/Al atomic ratio ranging from 2 to 18, wherein the first catalyst composition molecular sieve comprises a plurality of pores, with a shape of an 8-membered ring or less and further wherein the first catalyst composition molecular sieve in the first catalyst composition is SSZ-39; wherein the first product stream has a propylene to ethylene ratio of greater than 1, wherein the second reaction conditions of step (d) include a reaction temperature ranging from 500° C. to 600° C., wherein the cracking catalyst of the second catalyst composition comprises one or more molecular sieves selected from silicalites from the MFI family with a Si/Al atomic ratio of more than 100, crystalline silicate from the MFI family with a Si/Al atomic ratio of at least 180, crystalline silicate from the MEL family with a Si/Al atomic ratio ranging between 150 and 800, or combinations thereof.

2. The process according to claim 1, characterized in that the Si/Al atomic ratio of the first catalyst composition is ranging from 5 to 18.

3. The process according to claim 1, characterized in that said one or more molecular sieves in the first catalyst composition contain less than 1000 wt. ppm of noble metal as determined by XRF as based on the total weight of the one or more molecular sieves.

4. The process according to claim 1, characterized in that said one or more molecular sieves in the first catalyst composition contain less than 1000 wt. ppm of transition metals as determined by XRF as based on the total weight of the one or more molecular sieves.

5. The process according to claim 1, characterized in that said one or more molecular sieves in the first catalyst composition contain less than 1 wt. % of alkali metals as determined by XRF and as based on the total weight of the one or more molecular sieves.

6. The process according to claim 1, characterized in that said one or more molecular sieves in the first catalyst composition comprise one or more alkaline earth metal-containing materials.

7. The process according to claim 6, characterized in that said alkaline earth metal is selected from the group of beryllium, magnesium, calcium, strontium, barium, and any mixtures thereof.

8. The process according to claim 1, characterized in that said one or more molecular sieves in the first catalyst composition comprise between 0.1 wt. % and 7.0 wt. % of one or more phosphorus-containing materials as based on the total weight of the catalyst composition.

9. The process according to claim 1, characterized in that the one or more methyl halides comprise at least 50 wt. % of bromine as based on the total weight of said one or more methyl halides.

10. The process according to claim 1, characterized in that the one or more methyl halides are methyl bromides.

11. The process according to claim 1, characterized in that the step (c) further comprises separating from the first product stream (5) a C4+ stream (15) and the step (d) comprises subjecting said C4+ stream (15) to an olefin catalytic cracking with said second catalyst composition in a second reaction zone (7) under second reaction conditions to provide a second product steam (9).

12. The process according to claim 1, characterized in that said step (d) of contacting said first product stream (5) with said second catalyst composition is followed by a step (e) of performing a separation of ethylene and propylene from said second product stream (5).

13. The process according to any claim 1, characterized in that said process further comprises one or more of the following sub-steps:
  i. removing hydrogen halide from said first product stream (5) before the step (d) or from said second product stream (9) after the step (d);
  ii. recovering at least a part of the unreacted one or more methyl halides before or after the step (d);
  iii. removing aromatics from said first product stream (5) before the step (d) or from said second product stream (9) after the step (d).

* * * * *